US00PP17755P2

(12) United States Plant Patent
Hofmann

(10) Patent No.: US PP17,755 P2
(45) Date of Patent: May 22, 2007

(54) **NEW GUINEA *IMPATIENS* PLANT NAMED 'FISUPNIC SALMDEEP'**

(50) Latin Name: *Impatiens hawkeri*
Varietal Denomination: Fisupnic Salmdeep

(75) Inventor: Birgit Christa Hofmann, Benforf (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 11/330,835

(22) Filed: Jan. 12, 2006

(51) Int. Cl.
*A01H 5/00* (2006.01)

(52) U.S. Cl. ..... Plt./318

(58) Field of Classification Search ..... Plt./318
See application file for complete search history.

*Primary Examiner*—Anne Marie Grunberg
*Assistant Examiner*—Georgia Helmer
(74) *Attorney, Agent, or Firm*—Jondle & Associates P.C.

(57) ABSTRACT

A new New Guinea *Impatiens* plant particularly distinguished by very large, round, almost flat, uniform salmon-orange flowers, early flowering, uniform, deep green foliage, and a medium to tall plant habit that is round and bushy, is disclosed.

1 Drawing Sheet

Genus and species: *Impatiens hawkeri* W. Bull.
Variety denomination: 'Fisupnic Salmdeep'.

BACKGROUND OF THE NEW PLANT

The present invention comprises a new and distinct cultivar of New Guinea *Impatiens,* botanically known as *Impatiens hawkeri* W. Bull, and hereinafter referred to by the cultivar name 'Fisupnic Salmdeep'. The new cultivar originated from a hybridization made in the year 2002 in Hillscheid, Germany. The female parent was the proprietary New Guinea *Impatiens* plant 'K02-169-3' (unpatented), while the male parent was the proprietary New Guinea *Impatiens* plant 'K01-8608-33' (unpatented). The seeds produced by the hybridization were sown in a greenhouse in Portugal in the late Fall of 2002. A single plant selection was chosen for further evaluation and for asexual propagation in April 2003 in Moncarapacho, Portugal.

The new cultivar was created in 2002 in Hillscheid, Germany and has been asexually reproduced repeatedly by vegetative cuttings and tissue culture in Moncarapacho. Portugal and Hillscheid, Germany over a three-year period. 'Fisupnic Salmdeep' has not been observed under all possible environmental conditions. The present invention has been found to retain its distinctive characteristics through successive asexual propagations.

Plant Breeder's Rights for this cultivar were applied for in Switzerland on Mar. 30, 2005 and in Canada on Apr. 20, 2005.

SUMMARY OF THE INVENTION

The following are the most outstanding and distinguishing characteristics of this new cultivar when grown under normal horticultural practices in Hillscheid, Germany and Langley, British Columbia, Canada.

1. Uniform salmon-orange flower color;
2. Very large, round, almost flat flowers;
3. Uniform, deep green foliage;
4. Medium to tall, round and bushy plant habit; and
5. Early flowering response.

DESCRIPTION OF PHOTOGRAPH

This new New Guinea *Impatiens* plant is illustrated by the accompanying photograph which shows overall plant habit including blooms, buds, and foliage of the plant; the colors shown are as true as can be reasonably obtained by conventional photographic procedures. The photograph is of a whole plant about 13 to 14-weeks old, grown in a greenhouse in Hillscheid, Germany, in the Spring (May).

DESCRIPTION OF THE NEW CULTIVAR

The following detailed descriptions set forth the distinctive characteristics of 'Fisupnic Salmdeep'. The data which define these characteristics were collected from asexual reproductions carried out in Hillscheid, Germany. The plant history was taken on 12-week old plants which were planted as rooted cuttings in 12-cm pots in late February 2005, and then grown in a greenhouse at a minimum temperature of 16° C. Color readings were taken under natural light in the greenhouse. Color references are primarily to The R.H.S. Colour Chart of The Royal Horticultural Society of London (R.H.S.) (2001).

DETAILED BOTANICAL DESCRIPTION OF THE NEW PLANT

Classification:
*Family.*—Balsaminaceae.
*Botanical.*—*Impatiens hawkeri* W. Bull.
*Common name.*—New Guinea *Impatiens.*

Parentage:
*Female parent.*—'K02-169-3' a proprietary cherry-red flowered New Guinea *Impatiens* plant (unpatented).
*Male parent.*—'K01-8608-33' a proprietary light-red to cherry-red flowered New Guinea *Impatiens* plant (unpatented).

Growth:
*Growth and branching habit.*—Medium size, round, bushy, and well-branched; the growth is indeterminate, though weak after the beginning of flowering.

*Height.*—15.2 cm.
*Width.*—25.3 cm.
*Propagation.*—Terminal tips for cuttings.
*Time to produce a finished flowering plant.*—9 weeks for a 12-cm pot.
*Time to initiate and develop roots.*—18 days at 22° C.

Branches:
*Average number.*—5.3.
*Length of branches.*—11 cm to 13 cm.
*Internode length.*—3.0 cm to 5.0 cm.
*Diameter of branches.*—0.6 cm to 0.7 cm.
*Stem color.*—RHS 185A at the upper part and RHS 146B (dull-green) at the lower part.

Leaves:
*Arrangement.*—Primarily in whorls.
*Size.*—Length: 11.5 cm. Width: 4.6 cm.
*Shape.*—Elliptic.
*Margin.*—Slightly serrate, ciliated.
*Apex.*—Acuminate.
*Base.*—Acute.
*Color* (*mature leaves*).—Upper surface: About RHS 137C (deep medium-green). Lower surface: About RHS 138B (light-green).
*Color* (*immature leaves*).—Upper surface: Near RHS 143A. Lower surface: RHS 138B (light-green).
*Texture.*—Surface slightly glossy, smooth or faintly rippled.
*Venation color.*—Upper surface: RHS 51B, near the base. Lower surface: RHS 53A (deep-red).
*Variegation.*—None.
*Petioles.*—Length: 2.5 cm. Diameter: 0.3 cm to 0.4 cm. Color: Upper surface: RHS 53C. Lower surface: RHS 53A. Texture: Glabrous.

Flower buds:
*Shape.*—Ovoid.
*Size.*—Length: 2.6 cm. Diameter: 1.5 cm.
*Color.*—RHS 43B (orange-red).

Inflorescence:
*Blooming habit.*—9 weeks after planting of rooted cuttings.
*Inflorescence type.*—Flowers appear solitary in the leaf axils of the upper nodes of the stems.
*Number of flowers per node.*—6 to 8, in various stages of development.
*Flowering season.*—Indeterminate, mainly from March to October, depending on light intensity.
*Lastingness of individual blooms.*—Up to 12 days (in a greenhouse in the spring at 18° C.).
*Peduncle.*—Color: RHS 184A (brownish-purple). Size: Length: 5.0 cm. Diameter: 0.1 cm. Texture: Glabrous, flexible.

Flowers:
*Form of corolla.*—Single-type, 5 petals.
*Shape of corolla.*—Round, with the petal overlapping, almost flat to slight butterfly-shape, outdoors weakly cup-shaped.
*Corolla size.*—Length: 8.3 cm. Width: 8.2 cm. Depth: 1.2 cm to 1.5 cm.

Petals:
*Shape.*—Cordate, weakly lobed at the top end.
*Apex.*—Retuse.
*Base.*—Attenuate.
*Margin.*—Entire.
*Petal size.*—Top: Length: 3.8 cm. Width: 6.5 cm. Lateral: Length: 4.0 cm. Width: 5.1 cm. Lower: Length: 4.0 cm. Width: 5.4 cm.
*Color.*—General color description: Orange, relatively uniform. Upper surface: RHS 41A, may turn to RHS 43C, no distinct markings. Lower surface: RHS 43C. Eye Zone: Very weak infusion of RHS N57B (purple).
*Petal texture.*—Smooth, velvety.
*Aspect.*—Flat.

Spur:
*Shape.*—Downwardly curved.
*Color.*—RHS 53C (reddish).
*Size.*—Length: 5.5 cm. Diameter: 0.3 cm (at the flower end).

Reproductive organs:
*Stamens.*—Number: 5 fused. Diameter: 0.5 cm to 0.6 cm. Stamen color (upper surface color): RHS 40A. Anthers: Fused, hooded. Pollen color: RHS 8D (whitish-yellow).
*Pistils.*—Style and sigma: 5, very short, RHS 150D (pale-yellow). Ovary: 5-celled. Ovary length: 0.5 cm. Ovary color: RHS 143A (surface green).

Fruit and seed set: No seed set observed.

Disease and insect resistance: No particular resistance or susceptibility has been observed.

COMPARISON WITH PARENTAL AND COMMERCIAL CULTIVARS

'Fisupnic Salmdeep' differs from the female parent 'K02-169-3' (unpatented), by having a salmon-orange flower color, while 'K02-169-3' has light cherry-red flowers. Additionally, 'Fisupnic Salmdeep' has larger flowers and a stronger branching habit than 'K02-169-3'.

'Fisupnic Salmdeep' differs from the male parent 'K01-8608-33' (unpatented), by having salmon-orange flowers and a taller plant habit, while 'K01-8608-33' has light red to cherry red flowers and a medium size plant habit.

'Fisupnic Salmdeep' differs from the commercial cultivar 'Fisupnic Salmon' (U.S. Plant Pat. No. 14,727) by having less intense orange-red flowers and larger flowers than 'Fisupnic Salmon'. Additionally, 'Fisupnic Salmdeep' has a lighter green foliage color (RHS 137C compared to RHS 139A) with light green undersides, while 'Fisupnic Salmon' has leaves with marbled light green and purple undersides. Also, 'Fisupnic Salmdeep' has shorter leaves and a tighter plant habit with shorter internodes.

'Fisupnic Salmdeep' differs from cultivar 'Fisnics Dark Salmon' (U.S. Plant Pat. No. 13,232) by having medium green leaves with light green undersides and a taller plant habit, while 'Fisnics Dark Salmon' has dark green leaves with reddish undersides. Additionally, 'Fisupnic Salmdeep' develops only a very weak purple eye to no eye, while 'Fisnics Dark Salmon' has strong purple eyes.

I claim:

1. A new and distinct cultivar of New Guinea *Impatiens* plant as shown and described herein.

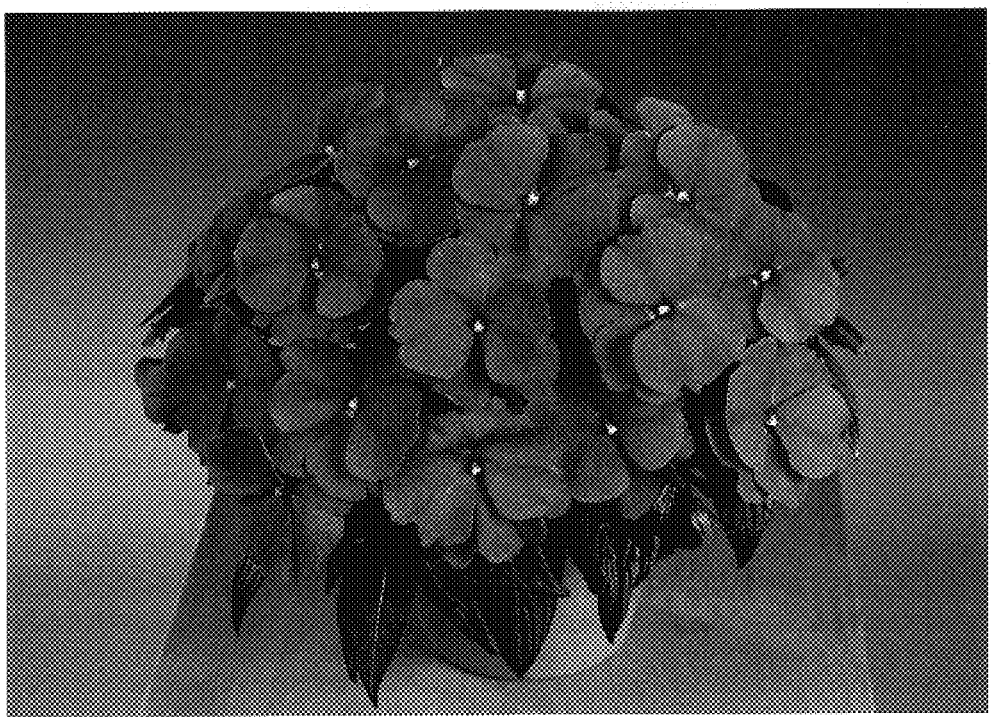

* * * * *